United States Patent
Bachynsky et al.

(10) Patent No.: US 9,642,911 B2
(45) Date of Patent: May 9, 2017

(54) PHARMACEUTICAL DOSAGE FORMS COMPRISING VALGANCICLOVIR HYDROCHLORIDE

(71) Applicant: Hoffmann-La Roche Inc., Little Falls, NJ (US)

(72) Inventors: Maria Oksana Bachynsky, Nutley, NJ (US); Martin Howard Infeld, Upper Montclair, NJ (US); Navnit Hargovindas Shah, Clifton, NJ (US)

(73) Assignee: Hoffmann-La Roche Inc., Little Falls, NJ (US)

(*) Notice: Subject to any disclaimer, the term of this patent is extended or adjusted under 35 U.S.C. 154(b) by 0 days.

(21) Appl. No.: 14/529,839

(22) Filed: Oct. 31, 2014

(65) Prior Publication Data
US 2015/0057296 A1   Feb. 26, 2015

Related U.S. Application Data

(63) Continuation of application No. 13/759,348, filed on Feb. 5, 2013, now Pat. No. 8,889,109, which is a continuation of application No. 12/001,290, filed on Dec. 11, 2007, now abandoned.

(60) Provisional application No. 60/874,634, filed on Dec. 13, 2006.

(51) Int. Cl.
  *A61K 47/12*   (2006.01)
  *A61K 47/10*   (2006.01)
  *A61K 31/522*  (2006.01)
  *A61K 9/00*    (2006.01)
  *A61K 9/16*    (2006.01)

(52) U.S. Cl.
  CPC ............ *A61K 47/12* (2013.01); *A61K 9/0095* (2013.01); *A61K 9/1623* (2013.01); *A61K 31/522* (2013.01); *A61K 47/10* (2013.01)

(58) Field of Classification Search
  None
  See application file for complete search history.

(56) References Cited

U.S. PATENT DOCUMENTS

| | | | |
|---|---|---|---|
| 6,083,953 A | 7/2000 | Nestor et al. | |
| 6,194,002 B1 | 2/2001 | Sherman | |
| 6,242,496 B1 * | 6/2001 | Kulkarni | A61K 47/12 514/649 |
| 6,365,196 B1 | 4/2002 | Venkatesh et al. | |
| 2002/0143058 A1 | 10/2002 | Safadi et al. | |

FOREIGN PATENT DOCUMENTS

| | | |
|---|---|---|
| EP | 0121901 | 10/1984 |
| EP | 1459739 | 9/2004 |
| WO | 97/27197 | 7/1997 |
| WO | 2005/021549 | 3/2005 |
| WO | 2005/087198 | 9/2005 |
| WO | 2007/022956 | 3/2007 |
| WO | WO 2007022956 * | 3/2007 ............... A61K 9/48 |

OTHER PUBLICATIONS

Stefanidis Valganciclovir in Aq Soln Drug Development and Industrial Pharm p. 879, 2005.*
(Columbian Off Act in Corres Columbian Appl. 09-053156 Sep. 11, 2012).
(Webpage http://www.transplantbuddies.org/library/drugs/valc.html).
(International Search Report for PCT/EP2007/063151 Oct. 1, 2008).
(Translation of Jap Off Act in Corres Jap Appl 2009540707 Apr. 17, 2012).
(Translation of Russian Office Action for Appl 2009126616 dated Oct. 20, 2010).
Anaizi et al., Am. J. Health-Syst-Pharm 59(13):1267-1270 (Jul. 2002).
Ansel et al. Pharmaceutical Dosage Forms and Drug Delivery Systems, (2004).
Chuieshov, I., Industrial Drug Production Technique 2:330 ( 1999).
Henkin, C et al., American Journal of Health-System Pharmacy 60(7):687-690 ( 2003).
"Material Safety Data Sheet for Valcyte Powder for Constitution, Edition: Feb. 22, 2005" pp. 2.
"Product Monograph of Valcyte, Valganciclovir Film Coated Tablets, Valganciclovir Powder for Oral Solution, Professed Standard, Antiviral Agent, Hoffman-La Roche Limited" pp. 12 (Jul. 21, 2014).
Stefandis et al., "Reactivity of Valganciclovir in Aqueous Solution" Drug Development and Industrial Pharmacy 31(9):879-884 ( 2005).

* cited by examiner

*Primary Examiner* — Suzanne Ziska
*Assistant Examiner* — Thurman Wheeler
(74) *Attorney, Agent, or Firm* — Genentech, Inc.; Mark D. Kafka

(57) ABSTRACT

The present invention provides novel solid pharmaceutical dosage forms for oral administration, after being constituted in water. The solid dosage forms comprise a therapeutically effective amount of valganciclovir hydrochloride and a non-hygroscopic organic acid present in an amount sufficient to stabilize the valganciclovir hydrochloride in a predetermined amount of water. The present invention also provides novel liquid pharmaceutical dosage forms for oral administration after constituting the solid pharmaceutical dosage form with water. A non-hygroscopic bulking agent may optionally be included in the above dosage form. These novel pharmaceutical dosage forms are useful in the treatment or control of viruses such as herpes simplex virus and cytomegalovirus. The present invention also provides a method for treating these diseases employing the solid and liquid pharmaceutical dosage forms and a method for preparing these pharmaceutical dosage forms.

1 Claim, No Drawings

PHARMACEUTICAL DOSAGE FORMS COMPRISING VALGANCICLOVIR HYDROCHLORIDE

PRIORITY TO RELATED APPLICATIONS

This application is a continuation application of U.S. application Ser. No. 13/759,348, filed Feb. 5, 2013, which is a continuation application of U.S. application Ser. No. 12/001,290, filed Dec. 11, 2007, which claims the benefit of U.S. Provisional Application No. 60/874,634, filed Dec. 13, 2006, each of which is hereby incorporated by reference in its entirety.

FIELD OF THE INVENTION

The present invention provides novel solid pharmaceutical dosage forms for oral administration, after being constituted in water. The solid dosage forms comprise a therapeutically effective amount of valganciclovir hydrochloride and a non-hygroscopic organic acid present in an amount sufficient to stabilize the valganciclovir hydrochloride in a predetermined amount of water. The present invention also provides novel liquid pharmaceutical dosage forms for oral administration after constituting the solid pharmaceutical dosage form with water. A non-hygroscopic bulking agent may optionally be included in the above dosage form. These novel pharmaceutical dosage forms are useful in the treatment or control of viruses such as herpes simplex virus and cytomegalovirus. The present invention also provides a method for treating these diseases employing the solid and liquid pharmaceutical dosage forms and a method for preparing these pharmaceutical dosage forms.

BACKGROUND OF THE INVENTION

Valganciclovir hydrochloride is a potent antiviral agent that has been approved for the treatment of cytomegalovirus (CMV) retinitis in patients with acquired immunodeficiency syndrome (AIDS) and for the prevention of CMV disease in kidney, heart, and kidney-pancreas transplantation. Valganciclovir hydrochloride is the L-monovaline ester of ganciclovir and is a stable prodrug of ganciclovir with improved absorption. Such characteristics are especially valuable for suppression of herpetic infections in immunocompromised patients where oral administration therapeutically is the preferred choice. Valganciclovir hydrochloride is described in detail in U.S. Pat. No. 6,083,953, which disclosure is incorporated by reference herein.

In the solid state, valganciclovir hydrochloride exhibits acceptable physical, chemical, and light stability when stored under ambient conditions. No special storage requirements are necessary except that excessive humidity must be avoided. Initial attempts to formulate a valganciclovir hydrochloride pediatric preparation and a formulation for patients who require flexibility of dosage focused on the development of an oral liquid product. However, short-term stability data indicated that a liquid dosage form would be unstable for the anticipated shelf life of the product. Accordingly, there is a need for a valganciclovir hydrochloride formulation for pediatric use and for patients who require flexibility of dosage.

SUMMARY OF THE INVENTION

The present invention provides a solid pharmaceutical dosage form for oral administration, after being constituted in water, comprising (a) a therapeutically effective amount of valganciclovir hydrochloride; and (b) a non-hygroscopic organic acid present in an amount sufficient to stabilize the valganciclovir hydrochloride in a predetermined amount of water.

The present invention also provides a liquid pharmaceutical dosage form for oral administration comprising (a) a therapeutically effective amount of valganciclovir hydrochloride; (b) a predetermined amount of water; and (c) a non-hygroscopic organic acid present in an amount sufficient to stabilize the valganciclovir hydrochloride in the predetermined amount of water.

The present invention further provides a method of treating a subject infected with a virus selected from the group consisting of herpes simplex virus and cytomegalovirus comprising administering to a patient, in need thereof, a therapeutically effective amount of a liquid pharmaceutical dosage form for oral administration comprising (a) a therapeutically effective amount of valganciclovir hydrochloride; (b) a predetermined amount of water; and (c) a non-hygroscopic organic acid present in an amount sufficient to stabilize the valganciclovir hydrochloride in the predetermined amount of water.

The present invention still further provides a method for preparing a solid pharmaceutical dosage form for oral administration, after being constituted in water, comprising admixing (a) a therapeutically effective amount of valganciclovir hydrochloride; and (b) a non-hygroscopic organic acid present in an amount sufficient to stabilize the valganciclovir hydrochloride in a predetermined amount of water.

DETAILED DESCRIPTION OF THE INVENTION

Initial attempts to formulate an appropriate dosage form of valganciclovir hydrochloride to treat pediatric patients and patients who require flexibility of dosage focused on the development of an oral liquid product. Short-term stability data indicated that liquid dosage forms are unstable for the anticipated shelf life of the product. Efforts therefore focused on powder dosage forms, for later constitution with water, to provide a reasonable shelf life for valganciclovir hydrochloride and the resulting (constituted) liquid dosage form. To improve the stability profile and manufacturability of the powder dosage form and the stability profile of the constituted liquid dosage form, the formulation procedure was changed from a dry mix granulation to a wet mix granulation.

Because valganciclovir hydrochloride is readily soluble under acidic conditions, a solid pharmaceutical dosage form must contain an organic acid present in an amount sufficient to solubilize and stabilize the valganciclovir hydrochloride in a predetermined amount of water for the proposed shelf life of the resulting (constituted) liquid dosage form. Hygroscopic organic acids were found to degrade the solid valganciclovir hydrochloride pharmaceutical dosage forms. Consequently, non-hygroscopic organic acids must be used in the solid pharmaceutical dosage forms. Optionally, a bulking agent may be included in the solid pharmaceutical dosage form to facilitate the manufacture of the solid pharmaceutical dosage form of the present invention. Bulking agents, such as crystalline maltose, were found to degrade the liquid (constituted) valganciclovir hydrochloride pharmaceutical dosage forms. Consequently, non-hygroscopic bulking agents, such as polyhydric alcohols in powder form, must be used in the solid pharmaceutical dosage forms.

The solid pharmaceutical dosage forms for oral administration, after being constituted in water, have the advantage of being able to provide the patient with the appropriate dosage level. For example, while valganciclovir hydrochloride is available as a 450 mg tablet for oral administration, liquid dosage forms may be prepared in a wide variety of concentration levels. A preferred liquid dosage form may be prepared at 50 mg/mL to provide a wide variety of dosage levels to treat pediatric patients and patients who require flexibility of dosage. The container for the liquid dosage form may be provided with a calibrated dispenser to dispense the appropriate amount of liquid containing the appropriate dosage level.

As used herein, the following terms have the given meanings:

The term "effective amount of a non-hygroscopic bulking agent" means an amount of a non-hygroscopic bulking agent sufficient to facilitate the manufacture of the solid pharmaceutical dosage form of the present invention. The presence of the non-hygroscopic bulking agent is optional but inclusion of the non-hygroscopic bulking agent makes the manufacturing process of preparing the solid pharmaceutical dosage form easier and can provide desirable bulk and sweetness in the final product.

The term "disease" specifically includes any unhealthy condition of a subject, as defined herein. Thus, "disease" herein includes any viral or related disease that is treatable with valganciclovir hydrochloride or pharmaceutically acceptable salts thereof.

The term "non-hygroscopic organic acid present in an amount to stabilize the valganciclovir hydrochloride in water" means that amount of non-hygroscopic organic acid necessary to lower the pH of the liquid pharmaceutical dosage form of valganciclovir hydrochloride and thereby stabilize the valganciclovir hydrochloride in the predetermined amount of water.

The term "pharmaceutically acceptable," such as pharmaceutically acceptable carrier, excipient, etc., means pharmacologically acceptable and substantially non-toxic to the subject in the quantity at which the particular compound is administered.

The term "pharmaceutically acceptable salt" refers to conventional acid-addition salts or base-addition salts that retain the biological effectiveness and properties of the compounds of the present invention and are formed from suitable non-toxic organic or inorganic acids or organic or inorganic bases. Sample acid-addition salts include those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, and the like. Sample base-addition salts include those derived from ammonium, potassium, sodium, and quaternary ammonium hydroxides, such as for example, tetramethylammonium hydroxide. Chemical modification of a pharmaceutical compound (i.e., drug) into a salt is a technique well known to pharmaceutical chemists to obtain improved physical and chemical stability and solubility of compounds. See, e.g., H. Ansel et. al., Pharmaceutical Dosage Forms and Drug Delivery Systems ($6^{th}$ Ed. 1995) at pp. 196 and 1456-1457.

The term "predetermined amount of water" means any desired amount of water to constitute the solid pharmaceutical dosage form of the present invention into a liquid pharmaceutical dosage form for oral administration. The amount of water can vary widely depending upon the desired concentration of the valganciclovir hydrochloride in the aqueous solution. The desired concentration of the valganciclovir hydrochloride in the aqueous solution may depend upon such factors as the particular subject being treated, the disease being treated, the length of time of the treatment, and the like.

The term "prodrug" refers to compounds which undergo transformation prior to exhibiting their pharmacological effects. The chemical modification of drugs to overcome pharmaceutical problems has also been termed "drug latentiation." Drug latentiation is the chemical modification of a biologically active compound to form a new compound, which upon in vivo enzymatic attack will liberate the parent compound. The chemical alterations of the parent compound are such that the change in physicochemical properties will affect the absorption, distribution and enzymatic metabolism. The definition of drug latentiation has also been extended to include nonenzymatic regeneration of the parent compound. Regeneration takes place as a consequence of hydrolytic, dissociative, and other reactions not necessarily enzyme mediated. The terms prodrugs, latentiated drugs, and bio-reversible derivatives are used interchangeably. By inference, latentiation implies a time lag element or time component involved in regenerating the bioactive parent molecule in vivo. The term prodrug is general in that it includes latentiated drug derivatives as well as those substances which are converted after administration to the actual substance which combines with receptors. The term prodrug is a generic term for agents which undergo biotransformation prior to exhibiting their pharmacological actions. Valganciclovir hydrochloride is a prodrug of ganciclovir.

The term "subject" includes humans, non-human mammals (such as dogs, cats, rabbits, cattle, horses, sheep, goats, swine, and deer) and non-mammals such as birds, fish and the like. Preferably the subject is a human or non-human mammal, and more preferably the subject is a human.

The term "therapeutically effective amount" with respect to valganciclovir hydrochloride means an amount of the compound, or a pharmaceutically acceptable salt thereof which, when administered to a subject in need thereof, is effective to treat, prevent, alleviate or ameliorate symptoms of disease.

The term "treatment" means any treatment of a disease in a subject and includes: (1) preventing the disease from occurring in a subject, who may be predisposed to the disease but does not yet experience or display symptoms of the disease e.g., prevention of the outbreak of the clinical symptoms; (2) inhibiting the disease, e.g., arresting its development; or (3) relieving the disease, e.g., causing regression of the symptoms of the disease.

The present invention provides a novel solid pharmaceutical dosage form for oral administration, after being constituted in water, comprising (a) a therapeutically effective amount of valganciclovir hydrochloride; and (b) a non-hygroscopic organic acid present in an amount sufficient to stabilize the valganciclovir hydrochloride in a predetermined amount of water.

The present invention also provides a novel liquid pharmaceutical dosage form for oral administration comprising (a) a therapeutically effective amount of valganciclovir hydrochloride; (b) a predetermined amount of water; and (c) a non-hygroscopic organic acid present in an amount sufficient to stabilize the valganciclovir hydrochloride in the predetermined amount of water.

The present invention further provides a novel method of treating a subject infected with a virus selected from the group consisting of herpes simplex virus and cytomegalovirus comprising administering to a patient, in need thereof, a therapeutically effective amount of a liquid pharmaceutical dosage form for oral administration comprising (a) a therapeutically effective amount of valganciclovir hydrochloride; (b) a predetermined amount of water; and (c) a non-hygroscopic organic acid present in an amount sufficient to stabilize the valganciclovir hydrochloride in the predetermined amount of water.

The present invention still further provides a method for preparing a solid pharmaceutical dosage form for oral administration, after being constituted in water, comprising admixing (a) a therapeutically effective amount of valganciclovir hydrochloride; and (b) a non-hygroscopic organic acid present in an amount sufficient to stabilize the valganciclovir hydrochloride in a predetermined amount of water.

Valganciclovir hydrochloride (valganciclovir HCl, Valcyte®) is a hydrochloride salt of the L-valyl ester (prodrug) of ganciclovir that exists as a mixture of two diastereomers. After oral administration, both diastereomers are rapidly converted to ganciclovir by intestinal and hepatic esterases. Ganciclovir is a synthetic analogue of 2'-deoxyguanosine, which inhibits replication of human cytomegalovirus in vitro and in vivo. Ganciclovir has been approved for the treatment of cytomegalovirus (CMV) retinitis in patients with acquired immunodeficiency syndrome (AIDS) and for the prevention of CMV disease in kidney, heart, and kidney-pancreas transplantation. Valganciclovir hydrochloride is available as a 450 mg tablet for oral administration. Each tablet contains 496.3 mg of valganciclovir hydrochloride (corresponding to 450 mg of valganciclovir), and the inactive ingredients microcrystalline cellulose, povidone K-30, crospovidone and stearic acid. The film-coat applied to the tablets contains Opadry® Pink.

Valganciclovir hydrochloride is a white to off-white crystalline powder with a molecular formula of $C_{14}H_{22}N_6O_5 \cdot HCl$ and a molecular weight of 390.83. The chemical name for valganciclovir hydrochloride is L-Valine, 2-[(2-amino-1,6-dihydro-6-oxo-9H-purin-9-yl)methoxy]-3-hydroxypropyl ester, monohydrochloride. The chemical structure of valganciclovir hydrochloride is set out below:

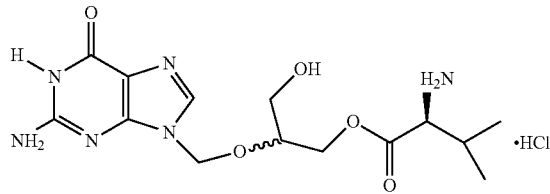 [SMILES: CC(C)[C@H](N)C(=O)OCC(CO)OCn1cnc2c(=O)[nH]c(N)nc21 ; Cl]

The solubility of valganciclovir hydrochloride (active pharmaceutical ingredient, API) in aqueous solution is pH dependent. Valganciclovir hydrochloride is a polar hydrophilic compound with a solubility of 70 mg/mL in water at 25° C. at a pH of 7.0 and an n-octanol/water partition coefficient of 0.0095 at pH 7.0. The pKa for valganciclovir hydrochloride is 7.6. Valganciclovir hydrochloride is freely soluble under acidic conditions with a maximum solubility of greater than 200 mg/mL in the pH range of 4-6. The stability of valganciclovir hydrochloride is greatest at a pH<3.8.

Valganciclovir hydrochloride can exist in one of two crystalline forms (termed X and Y) and an amorphous form. The commercial manufacturing process for the valganciclovir hydrochloride produces exclusively form Y. Form Y is stable with respect to the various pharmaceutical processes involved in the manufacture of the powder for oral solution. All valganciclovir hydrochloride lots used in the manufacture of formulation development, clinical, stability and registration batches were of form Y. For purposes of the present invention, any polymorphic or amorphous form of valganciclovir hydrochloride may be employed since the final formulation is liquid. Any diastereomer or mixture of diastereomers may also be used.

Valganciclovir hydrochloride is moderately hygroscopic, with only small changes in moisture observed when the valganciclovir hydrochloride is exposed to moderate relative humidity. A weight gain of up to approximately 3% occurs when the valganciclovir hydrochloride is exposed to 80% relative humidity (for a total moisture content of up to approximately 8%). It is reversibly hygroscopic and will either absorb or release moisture under ambient humidity conditions, depending on the water content of the valganciclovir hydrochloride and the relative humidity.

The therapeutically effective amount or dosage level of valganciclovir according to this invention can vary within wide limits. While valganciclovir hydrochloride is available as a 450 mg tablet for oral administration, solid pharmaceutical dosage forms which can be constituted into liquid pharmaceutical dosage forms can be prepared in a wide variety of concentration levels to accommodate pediatric patients and patients who require flexibility of dosage. The container for the solid/liquid dosage form may be provided with a calibrated dispenser to dispense the appropriate amount of liquid containing the appropriate dosage level. Such dosage levels can be adjusted to the individual requirements in each particular case regarding the patient and condition being treated.

In general, the amount of valganciclovir hydrochloride present in the solid pharmaceutical dosage form may range from about 10% to about 90%, preferably from about 25% to about 75%, more preferably from about 35% to about 60% and most preferably about 46%, by weight of the total composition.

In general, the liquid pharmaceutical dosage forms, which can be constituted from the solid pharmaceutical dosage forms using a predetermined amount of water, may be prepared at valganciclovir (as free base) concentration levels of from about 10 mg/mL to about 90 mg/mL, preferably from about 25 mg/mL to about 75 mg/mL, more preferably from about 35 mg/mL to about 65 mg/mL, and most preferably about 50 mg/mL.

The non-hygroscopic organic acids in the present invention may be selected from a wide variety of non-hygroscopic organic acids. As set out above, hygroscopic organic acids degrade the solid valganciclovir hydrochloride pharmaceutical dosage forms. A non-hygroscopic organic acid will absorb less than 1% of water by weight at about 60-75% relative humidity at ambient temperatures. In one embodiment, the non-hygroscopic organic acid is an amino acid. Preferably, the amino acid is aspartic acid or glutamic acid. In another embodiment, the non-hygroscopic organic acid is selected from the group consisting of fumaric acid, succinic acid, adipic acid. Preferably, the non-hygroscopic organic acid is fumaric acid or succinic acid. More preferably, the non-hygroscopic organic acid is fumaric acid.

The non-hygroscopic organic acid is present in an amount sufficient to stabilize the valganciclovir hydrochloride in the solid pharmaceutical dosage form. Valganciclovir hydrochloride has a solubility of 70 mg/mL in water at 25° C. at a pH of 7.0 and is freely soluble under acidic conditions with a maximum solubility of greater than 200 mg/mL in the pH range of 4-6. In general, the amount of non-hygroscopic organic acid will lower the pH of the constituted valganciclovir hydrochloride solution to a pH of <3.8, and most preferably to a pH of 3.0.

The solid pharmaceutical dosage form may optionally contain an effective amount of a non-hygroscopic bulking agent. As set out above, hygroscopic bulking agents degrade valganciclovir hydrochloride in solid pharmaceutical dosage forms. The presence of the non-hygroscopic bulking agent makes the manufacturing process of preparing the solid pharmaceutical dosage form easier and can provide desirable bulk and sweetness in the final product. The non-hygroscopic bulking agent in the present invention may be selected from a wide variety of non-hygroscopic bulking agents. A non-hygroscopic bulking agent will absorb less than 1% of water by weight at about 60-75% relative humidity at ambient temperatures. In general, the non-hygroscopic bulking agent is selected from the group consisting of mannitol and lactose. Preferably the non-hygroscopic bulking agent is mannitol.

The non-hygroscopic bulking agent may be present in the solid pharmaceutical dosage form in an amount from about 10% to about 90%, preferably from about 30% to about 70%, and more preferably from about 40% to about 60%, by weight of the total composition.

A preferred embodiment of the present invention is set out in Table 1. The solid pharmaceutical dosage form for oral administration is a powder, which is constituted with a predetermined amount of purified water, to provide a liquid pharmaceutical dosage form. The bottle contains about 5.515 g of valganciclovir hydrochloride in a total of 12 g of powder for constitution into a solution for oral administration. When constituted, the volume of the solution is 100 mL. A quantity of 1 mL of the constituted solution contains 55.15 mg of valganciclovir hydrochloride corresponding to 50 mg of valganciclovir free base. The concentration of the valganciclovir, as free base, in the constituted solution is 5.0%. The valganciclovir hydrochloride and the excipients are soluble in the aqueous vehicle. The powder blend may be manufactured by conventional pharmaceutical processes including wet granulation. The product is preferably marketed in amber glass bottles with child-resistant plastic screw caps.

TABLE 1

Pharmaceutical Composition of Valganciclovir Hydrochloride as Powder and Constituted Solution
Formulation Number F01

| Components | Unit Weight mg/120 mg | Filling Mixture g/bottle | Constituted Soln mg/mL |
|---|---|---|---|
| Valganciclovir HCl | 55.15[1] | 5.515[1] | 55.15[1] |
| Povidone K30 | 2.00 | 0.200 | 2.00 |
| Fumaric Acid | 2.00 | 0.200 | 2.00 |
| Sodium Benzoate | 1.00 | 0.100 | 1.00 |
| Sodium Saccharin | 0.25 | 0.025 | 0.25 |
| Mannitol | 57.80 | 5.780 | 57.80 |
| Tutti-Frutti Flavor | 1.80 | 0.180 | 1.80 |
| Purified Water | [2] | [2] | 0.91 mL |
| Total | 120 mg | 12.000 g | 1.000 mL |

[1]Equivalent to 50 mg of valganciclovir (as free base) on dry basis (HCl salt = MW 390.83; Base = MW 354.36)
[2]Removed during processing The pharmaceutical dosage forms of the present invention can be prepared according to the examples set out below. The examples are presented for purposes of demonstrating, but not limiting, the preparation of the compounds and compositions of this invention.

EXAMPLES

In accordance with the present invention, the following examples are provided to illustrate solid and liquid pharmaceutical dosage forms.

Example 1

A comparison of valganciclovir hydrochloride formulations of Type I and Type II is set out below in Table 2.

TABLE 2

Powder for Oral Solution—Comparison of Formulations

| | Type I mg/250 mg (constituted = 1 mL) | Type II mg/120 mg (constituted = 1 mL) | |
|---|---|---|---|
| | Formulation Number | | |
| Ingredients | J05 | F01-03 | F01-02 |
| Valganciclovir Hydrochloride | 55.15[1] | 55.15[1] | 55.15[1] |
| Citric Acid Anhydrous | 9.50 | — | — |
| Sodium Citrate | 0.40 | — | — |
| Sodium Benzoate | 1.00 | 1.00 | 1.00 |
| Fumaric Acid | — | 2.00 | 2.00 |
| Povidone K30 | — | 2.00 | 2.00 |
| Sodium Saccharin | 0.25 | 0.25 | 0.25 |
| Strawberry Flavor #E187196 | 5.00 | — | — |
| Tutti-Frutti Flavor #11900-31 | — | 1.80 | 1.80 |
| Maltose, Crystalline | 178.70 | — | — |
| Mannitol | — | 57.80 | 57.80 |
| Purified Water | — | [2] | [2] |
| Total weight per mL | 250.00 mg | 120.00 mg | 120.00 mg |
| Bottle Fill Weight | 15.00 g | 14.40 g | 12.00 g |
| Amount of water to be added | 51 mL | 109 mL | 91 mL |
| Total Constituted Volume | 60 mL | 120 mL | 100 mL |
| Bottle: Type I amber glass | 120 mL | 120 mL | 120 mL |

[1]Equivalent to 50 mg of valganciclovir (as free base) on a dry basis
[2]Removed during processing Type I Formulations The following excipients were used to prepare the formulations of Type I. Citric acid anhydrous was combined with sodium citrate to form the buffer system to ensure an acidic pH. The acidic pH helps stabilize valganciclovir since valganciclovir shows the greatest stability in an aqueous solution at a pH value of about 3.8 or below. Sodium benzoate was used as a preservative agent and sodium saccharin was used as an artificial sweetening agent. Maltose, a crystalline disaccharide carbohydrate, was used as a bulking agent (diluent) and to provide desirable mouth feel and sweetness. Strawberry flavor was used as the flavor of the oral solution.

The following procedure was used for the preparation of the Type I, Formulation J05. In step 1, sodium citrate and sodium saccharin were screened separately and blended with a portion of the crystalline maltose in a mixer. In step 2, the mixture from step 1 was blended with milled citric acid anhydrous and another portion of crystalline maltose, and strawberry flavor. In step 3, the blended material was screened and blended with screened sodium benzoate and a portion of the crystalline maltose. In step 4, the remainder of the crystalline maltose and valganciclovir hydrochloride was blended with the blended material from step 2 and this blended material was then screened. The blended material from step 3 was sandwiched between two layers of the screened material from step 4 and mixed into the final blend. A quantity of 15 g of the final blend was filled into each bottle and capped with the designated closure.

Example 2

Type II Formulations

The reason for changing the formulation from Type I to Type II and within Type II was to improve the stability profile of the solid pharmaceutical dosage form and the constituted liquid pharmaceutical dosage form for oral administration. The differences between the Type I and the Type II formulations are set out below.

Degradation was observed in the Type I formulation and was attributed to valganciclovir hydrochloride/citric acid interaction in the solid pharmaceutical dosage form. Citric acid is a hygroscopic organic acid and appears to degrade valganciclovir hydrochloride in the solid dosage form. Fumaric acid, a less hygroscopic organic acid, was therefore selected to replace citric acid/sodium citrate in the Type II formulations.

Degradation was also observed in the Type I formulation and was attributed to valganciclovir hydrochloride/maltose interaction in the constituted liquid pharmaceutical dosage form for oral administration. Maltose appears to degrade valganciclovir hydrochloride in the liquid dosage form. Maltose was replaced by mannitol, a polyhydric alcohol, which did not result in the degradation of valganciclovir hydrochloride. Povidone K30 (polyvinylpyrrolidone) was added as a binder and water as a granulating liquid to change the manufacturing process from a dry mix to a wet granulation process. The introduction of the wet granulation process considerably increased the flow properties of the filling mixture of the Type II formulation. Tutti-Frutti flavor replaced strawberry flavor in the proposed market formulation. The total weight of powder per bottle changed from 15.00 g, Formulation J05 (Type I), to 14.40 g, Formulation F01-03 (Type II). The proposed market formulation weight, Formulation F01-02 (Type II), was then decreased to 12.00 g to allow more headspace in the bottle for shaking to effect constitution.

Example 3

Manufacturing Process for Type II Formulations

The batch manufactured for the clinical Type I formulation was initially based on a dry powder mixture. Upon reformulation with different excipients, the flow properties of the final powder mix were found to be insufficient for appropriate performance. By using wet granulation, the flow properties of the final powder were considerably improved. Since commercial valganciclovir 450 mg tablets utilize an aqueous wet granulation process with povidone K30 as the binder, this process served as the basis for the preparation of the solid pharmaceutical dosage form for constitution with a predetermined amount of water.

In the present process, the active substance is preblended with povidone K30, fumaric acid, and mannitol. Sodium benzoate and sodium saccharin were dissolved in purified water which served as the granulation solution. The granulation is prepared in a high shear mixer. The flavor is added to the dried and milled granulates during the final blending to form the filling mixture. Development processing variables included with and without binder and its order of addition and the order of addition of sodium benzoate and sodium saccharin.

The granulation was very weak without a binder and milling produced an excessive amount of fines. There was no difference between adding the binder (povidone K30) as a granulating solution or adding it dry. For processing ease, povidone K30 was added dry.

Sodium benzoate and sodium saccharin were added to the final milled granulate as dry powders as well as dissolved in purified water prior to the granulating step. Chemical analysis for sodium benzoate and its content uniformity showed that incorporation of the preservative into the solution and granulating the powders with a high shear mixer resulted in a % RSD (relative standard deviation) of the preservative of <2%. Addition of dry sodium benzoate into the final powder blend created unacceptable variability. It is critical to rinse the granulating solution container thoroughly with a portion of purified water to assure the quantitative transfer of all of the sodium benzoate.

Example 4

Stability Batches

Stability data of representative lots of Type I and Type II formulations are presented in Table 3 (as powder for constitution) and Table 4 (as constituted solution). Type II powder and Type II constituted solution show a better stability profile in terms of recovery of valganciclovir and amount of total impurities.

TABLE 3

Powder for Oral Solution—Comparison of Stability Data

| | Formulation | | | |
|---|---|---|---|---|
| | Type I Powder Formulation J05 Lot C200860 | | Type II Powder Formulation F01-02 Lot P000024 | |
| Storage Conditions | Assay (% Label Claim) valganciclovir | Total Impurities | Assay (% Label Claim) valganciclovir | Total Impurities |
| Initial | 100.4% | 1.4% | 102.1% | 1.1% |
| 12 months 25° C./60% RH | 99.4% | 2.0% | 100.0% | 1.2% |
| 18 months 25° C./60% RH | 98.9% | 2.9% | 100.0% | 1.3% |

TABLE 3-continued

Powder for Oral Solution—Comparison of Stability Data

| | Formulation | | | |
|---|---|---|---|---|
| | Type I Powder Formulation J05 Lot C200860 | | Type II Powder Formulation F01-02 Lot P000024 | |
| Storage Conditions | Assay (% Label Claim) valganciclovir | Total Impurities | Assay (% Label Claim) valganciclovir | Total Impurities |
| 24 months 25° C./60% RH | 96.9% | 4.3% | 101.9% | 1.4% |

TABLE 4

Constituted Solution—Comparison of Stability Data

| | Formulation | | | |
|---|---|---|---|---|
| | Type I Constituted Solution Formulation J05 Lot C200860 | | Type II Constituted Solution Formulation F01-02 Lot P000024R | |
| Storage Conditions | Assay (% Label Claim) valganciclovir | Total Impurities | Assay (% Label Claim) valganciclovir | Total Impurities |
| Initial | 100.0% | 1.42% | 102.1% | 1.1% |
| 1 month 5° C. | 99.9% | 1.69% | 97.0% | 1.1% |
| 2 months 5° C. | 99.9% | 2.20% | 98.1% | 1.2% |
| 3 months 5° C. | Not available | Not available | 99.2% | 1.3% |

Process Optimization

Two demonstration batches of valganciclovir powder for constitution were prepared. The first demonstration batch (series 1) was manufactured to evaluate the manufacturing process at the 5 Kg scale. This batch was hand filled into bottles. No significant issues were observed during the preparation of the batch. The second demonstration batch (series 2) was manufactured to evaluate the manufacturing process at the 17.25 Kg scale. The focus of the second batch was to evaluate the mechanical bottle-filling step. The granulation, drying and blending steps for this demonstration batch were successfully executed. Powder filling trials utilizing an auger filler were successful. Bottle fill weight was maintained at all times throughout the entire study without complications.

The valganciclovir powder manufacturing process optimization (batch size 30 Kg) consisted of dry mixing, granulation solution addition, wet granulation, wet milling, fluidized bed drying, dry milling, blending and bottle filling. A total of 9 development batches (batch numbers 283, 293, 303, 313, 323, 333, 463, 473, and 493) were manufactured at production scale to optimize the parameters for each manufacturing step for valganciclovir powder for constitution.

Manufacturing Process

Valganciclovir hydrochloride, mannitol (Parteck M200), povidone K30, and fumaric acid were placed in a high shear mixer/granulator and dry mixed. After dry mixing, the granulating solution was added to the high shear granulator. The granulating solution consisted of sodium benzoate, sodium saccharin, and purified water and was prepared prior to the start of the dry mixing step. It is critical to transfer all of the granulating solution to ensure 100% recovery of sodium benzoate in the final product. From the granulator, the wet granulation was milled through a Fitzmill to improve material flow and transferred to a fluid bed dryer. A comparison was made between milling and not milling the wet granulation. From the dryer, the dried granulation was milled through a Fitzmill. The granulation was then blended with premixed flavor. A comparison was made between premixing the flavoring versus adding the flavor to the blend directly. The powder blend was then bottle filled and packaged. Material additions and transfers during the manufacturing process were performed via a vacuum transfer system.

The following process parameters were monitored and evaluated during the development work.
(a) dry mix granulation (blend particle size distribution);
(b) wet granulation [volume of water in granulation solution, solution addition rate (182-558 g/min)] to a granulation endpoint (time, Kw, visual);
(c) fluid bed drying, [drying endpoint
(d) dry milling at a speed of 1000-4500 rpm;
(e) final blending [final blend time (addition of flavor), 5-15 minutes, uniformity of dose units, active pharmaceutical ingredient and preservative assays, sieve analysis, bulk and tapped density];
(f) bottle filling (auger speed, 400-800 rpm);
(g) flow determination; powder flow was assessed by evaluation of packing properties through bulk density determination. The Carr Index (CI) values were used to evaluate the flow of dry milled, final blend and bottle filling samples and were calculated using the following equation;

$$CI = \frac{\text{Tap Density} - \text{Bulk Density}}{\text{Tap Density}} \times 100$$

The CI values for dry milling samples ranged from 12.66 to 39.19, indicating that the flow behavior was good to very poor. Batch #473, which had the largest amount (28%) of particles between 250-425μ, possessed the best flow, while batch #323, which had the largest amount (38%) of fine particles (<75μ), possessed the worst flow among nine batches.

Different particle size distribution profiles for dry milling were observed in all batches. These results are attributed to the fact that the granulation processes were varied in each batch (i.e., granulation solution volume, addition time, delivery rate, feed rate, discharge rate, etc.).

Observations

Particle size distribution profiles of the final blend for batches #303 and #493 were in good agreement with data from sieve analysis for the second demonstration batch.

There were slightly more fine particles (<75μ) in batches #303 and #493 compared to the second demonstration batch. Water utilized in the granulation solution was in the range of 2.7 to 3.45 Kg for both batches. Addition time of the granulation solution was in the range of 4-5.5 minutes. Wet mass time was 1.5 to 2 minutes. Drying endpoint (LOD) of sample port samples were in the range of 1.8 to 2.13%.

The CI values for final blend samples ranged from 17.44 to 33.80, indicating that the flow behavior was fair to very poor. Batches #283, #293, and #473, which contained larger amounts of 250μ size particles, exhibited better flow than the batches containing larger amounts of fine particles.

Within a batch, there was no significant difference between the flow of start, middle or end for the bottle filling samples of batch #283 or #293. Slight differences in flow property were observed between both batches. The CI values ranged from 19.10 to 24.18, indicating fair flow property.

Analytical Assay Results

All batches had acceptable content uniformity with % RSD (relative standard deviation) values lower than the acceptance criteria of ≤5.0%.

The average analytical assay value for sodium benzoate in batch #293 was 85.5%, which was within an acceptance criteria limit. Water rinsing of the sodium benzoate container was not performed in this batch, which may have resulted in a loss of sodium benzoate. Therefore, a rinsing step is necessary to ensure complete transfer of sodium benzoate.

Batches #303 and #323 used 1.7 Kg of water to prepare the granulation solution. Both batches produced had low levels of sodium benzoate. This may have resulted from an insufficient amount of water to dissolve the sodium benzoate. Therefore, a larger amount of water would be needed to ensure that all of the sodium benzoate was in solution.

The blend time study for batch #333 indicated that sodium benzoate and valganciclovir exhibited good content uniformity at all time points investigated (5, 7.5 and 10 minutes). However, blend time data for batch #493 indicated that valganciclovir had better content uniformity at 5 and 10 minutes while sodium benzoate had better content uniformity at 7.5 and 10 minutes. Based on these data, a blend time of 10 minutes was selected to ensure that good content uniformity would be obtained for both valganciclovir and sodium benzoate. The flavor premix in batch #283 did not result in significant improvement in the flavor's content uniformity in the product. Therefore, the flavor premix step would not be included in the final process. Bottle filling was accomplished using an All-Fill Servometer Filling machine.

Overall, physical and analytical data were acceptable for all batches. Greater weight fluctuation of the final powder blend was observed in batch #323 when an auger speed of 600 rpm was used to fill the bottles. Therefore, an auger speed of 450 rpm was selected for the filling process.

Manufacturing Process Recommendation for Registration Batches

For a dry mix procedure, mannitol (Parteck M200), povidone K30, fumaric acid powder, and valganciclovir hydrochloride were charged to a PMA 65 granulator and dry mixed for 7 minutes at an impeller speed of 200±50 rpm and chopper speed of 1000±50 rpm. For solution addition and wet granulation, a total of 3.45 Kg of water (granulation solution and rinse) is required for the granulation process. The granulation solution is to be added to the PMA 65 for 4±0.5 minutes at an impeller speed of 200±50 rpm and chopper speed of 1000±50 rpm. The wet mass should be mixed for an additional 1±0.5 minutes at the same impeller and chopper settings. Wet milling is not required.

For drying, the granulation from the PMA 65 was then charged to a fluid bed dryer and dried to an LOD of 1.3 to 3.0% with a target of 2.25%. The target product temperature is 50° C. (acceptable range 48°-52° C.). For milling, the dried granules were milled through a Fitzmill at a speed of 2400±50 rpm, using a #0 plate with knives forward. For blending, a flavor pre-mix is not required. The milled granules are to be blended with the tutti frutti flavor in a 3 cu ft tote bin blender for 10 minutes at a setting of 10 rpm. An All-Fill Powder Filling Machine was used to fill the product into the bottles with an auger speed of 450 rpm and dribble speed of 100 rpm.

A total of three registration batches (batches #024, #034 and #044) were manufactured at production scale (30 Kg) to evaluate the parameters established for each manufacturing step of valganciclovir powder for constitution. The bulk and tap densities of the final blends for batches #024, 034 and 044 were similar. All batches exhibited fair to poor flow properties for the final blend (Carr Index values 21.79 to 31.46).

Analytical assay results for valganciclovir and sodium benzoate for batches #024, #034 and #044 were within acceptance criteria limits. Blend uniformity ranged from 96.4% to 102.9% for valganciclovir and 96.4% to 100.0% for sodium benzoate. The % RSD was in the range of 0.3 to 1.2% for valganciclovir and sodium benzoate. All analytical results indicated acceptable content uniformity with % RSD values lower than the validation acceptance criteria of ≤5.0%.

Three registration batches of valganciclovir powder for constitution were successfully manufactured using process parameters established from developmental batches. All three batches met acceptance criteria limits. In-process and analytical data collected indicated that the manufacturing process is well controlled and able to provide consistent product quality in accordance with current GMP standards.

Efficacy of Preservative

The constituted solution contains sodium benzoate in a concentration of 0.1%. This solution has satisfactory bactericidal and fungicidal preservative effectiveness in glass bottles, which ensures that acceptable antimicrobial efficacy will be present throughout the use period of the product.

Comparative Bioavailability of the Clinical Formulation Versus the Market Formulation The primary objective of this study was to determine the bioequivalence of ganciclovir from the valganciclovir tutti-frutti oral solution (F01-02) and Valcyte®, the 450 mg marketed tablet formulation of valganciclovir hydrochloride, at a dose of 900 mg administered in the non-fasting state. The secondary objective was to compare the systemic exposure of ganciclovir from the valganciclovir strawberry flavored oral solution (J05) with the valganciclovir tutti-frutti flavored oral solution (F01-02) at a dose of 900 mg.

For both AUC 0-24 (area under the curve from 0-24 hours) and Cmax (maximum peak concentration), the 90% confidence interval (CI) for the mean ratios of the tablet relative to the tutti-frutti flavored oral solution lies entirely within the acceptance region of 80% to 125% ([96, 104] and [89, 101] for AUC 0-24 and Cmax, respectively). Bioequivalence of the tablet and the tutti-frutti flavored oral solution with respect to ganciclovir plasma levels can therefore be concluded. Based on the average ganciclovir AUC values, the tutti-frutti flavored oral solution delivers similar exposures known to be safe and efficacious. The ganciclovir PK comparing the tutti frutti flavored formulation vs. the strawberry flavored formulation is very similar in terms of Cmax and AUC resulting in 90% CI for the mean ratios of 96% to 109% and 94% to 101%, respectively.

While a number of embodiments of this invention have been represented, it is apparent that the basic construction can be altered to provide other embodiments that utilize the invention without departing from the spirit and scope of the invention. All such modifications and variations are intended to be included within the scope of the invention as defined in the appended claims rather than the specific embodiments that have been presented by way of example.

The invention claimed is:

1. A liquid pharmaceutical dosage form for oral administration, wherein the dosage form has the following composition:

| Components | Constituted Soln Per mL |
|---|---|
| Valganciclovir HCl | 55.15 mg[1] |
| Povidone K30 | 2.00 mg |
| Fumaric Acid | 2.00 mg |
| Sodium Benzoate | 1.00 mg |
| Sodium Saccharin | 0.25 mg |
| Mannitol | 57.80 mg |
| Tutti-Frutti Flavor | 1.80 mg |
| Purified Water | 0.91 mL |

[1]Equivalent to 50 mg of valganciclovir (as free base) on a dry basis.

* * * * *